(12) United States Patent
Bornzin et al.

(10) Patent No.: US 7,024,241 B1
(45) Date of Patent: Apr. 4, 2006

(54) PACING PULSE WAVEFORMS THAT SUPPORT SIMULTANEOUS INTRACARDIAC SIGNAL SENSING AND ANALYSIS

(75) Inventors: Gene A. Bornzin, Simi Valley, CA (US); Peter Boileau, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 522 days.

(21) Appl. No.: 10/313,684

(22) Filed: Dec. 5, 2002

(51) Int. Cl.
  *A61N 1/362* (2006.01)
(52) U.S. Cl. .......................................... 607/9
(58) Field of Classification Search ............... 607/4–28
  See application file for complete search history.

(56) References Cited

U.S. PATENT DOCUMENTS

| | | | |
|---|---|---|---|
| 4,686,988 A | 8/1987 | Sholder | 128/419 PT |
| 4,708,142 A | 11/1987 | DeCote, Jr. | 128/419 PT |
| 4,712,555 A | 12/1987 | Thornander et al. | 128/419 PG |
| 4,729,376 A | 3/1988 | DeCote, Jr. | 128/419 PT |
| 4,788,980 A | 12/1988 | Mann et al. | 128/419 PG |
| 4,809,697 A | 3/1989 | Causey, III et al. | 128/419 PT |
| 4,940,052 A | 7/1990 | Mann et al. | 128/419 PG |
| 4,944,298 A | 7/1990 | Sholder | 128/419 PG |
| 4,944,299 A | 7/1990 | Silvian | 128/419 PG |
| 4,969,467 A | 11/1990 | Callaghan et al. | 128/419 PG |
| 5,184,616 A | 2/1993 | Weiss | 128/419 |
| 5,188,106 A * | 2/1993 | Nappholz et al. | 607/24 |
| 5,350,410 A | 9/1994 | Kleks et al. | 607/28 |
| 5,466,254 A | 11/1995 | Helland | 607/123 |
| 5,476,483 A | 12/1995 | Bornzin et al. | 607/17 |
| 5,573,550 A | 11/1996 | Zadeh et al. | 607/28 |
| 5,685,315 A | 11/1997 | McClure et al. | 128/708 |
| 6,044,294 A | 3/2000 | Mortazavi et al. | 600/547 |
| 2001/0049543 A1 * | 12/2001 | Kroll | 607/28 |
| 2002/0077666 A1 | 6/2002 | Sherman | 607/5 |

FOREIGN PATENT DOCUMENTS

| | | |
|---|---|---|
| EP | 0281219 A1 | 1/1988 |
| EP | 0281219 B1 | 1/1988 |
| WO | WO 02/49712 A2 | 6/2002 |

* cited by examiner

*Primary Examiner*—Scott M. Getzow

(57) ABSTRACT

An implantable cardiac stimulation device is configured to generate multiphasic stimulation pulse waveforms. These multiphasic stimulation pulse waveforms are configured such that they can be substantially rejected within the intracardiac signal sensing circuitry. In certain implementations this allows for simultaneous stimulation therapy and sensing and analysis of intracardiac signals. In other implementations, the blanking interval associated with the intracardiac signal sensing circuitry may be reduced or eliminated. Furthermore, the fast recharge period may be reduced or eliminated, and/or the polarization at lead-tissue interface may be reduced or effectively eliminated by using multiphasic stimulation pulse waveforms. Such cardiac stimulation techniques are particularly useful in providing antitachycardia pacing (ATP) therapy, wherein pacing during a T wave can lead to fibrillation being triggered.

20 Claims, 5 Drawing Sheets

PACING PULSE WAVEFORMS THAT SUPPORT SIMULTANEOUS INTRACARDIAC SIGNAL SENSING AND ANALYSIS

TECHNICAL FIELD

The present invention generally relates to methods and arrangements for providing cardiac pacing therapy. More particularly, the invention concerns improved methods and arrangements for providing stimulation pulse waveforms that do not significantly interfere with simultaneous intracardiac signal sensing and analysis.

BACKGROUND

Implantable pacing devices, such as, e.g., pacemakers, are used to treat a variety of cardiac conditions. Some pacemakers simply provide pacing pulses to a patient's heart at a fixed rate. More sophisticated devices contain sensing circuitry that allows the pacemaker to monitor a patient's heartbeat signals. For example, some pacemakers can monitor a patient's atrial heartbeat signals and provide corresponding ventricular pacing pulses, which allows the patient's cardiac output to be adjusted depending on the patient's intrinsic atrial heart rate.

Thus, certain therapy methods require that electrical activity in one area of the heart be sensed and analyzed while the same area or other areas of the heart are stimulated. For example, one area of the heart may be stimulated by high rate antitachycardia pacing (ATP) pulses. Unfortunately, these and other stimulation pulses can interfere with the sensing and analysis of the heart's electrical activity.

A similar problem exists in bradycardia pacemakers. For example, in dual chamber modes, the ventricular channel must be alert to sense R-waves while the atrial channel stimulates the atrium. In conventional pacemakers, this problem is typically addressed by blanking the sense amplifiers (e.g., disconnecting their inputs from the pacing/sensing electrodes) during a stimulation pulse and its associated fast recharge phase.

Blanking sense amplifiers may not be an adequate solution for sensing during ATP for several reasons. First, intervals between ATP pulses are typically very short (e.g., about 20 milliseconds during a 50 Hz burst). Therefore, the amount of time during which an amplifier is blanked for each pulse (e.g., about 12 milliseconds) is relatively long when compared to the time during which it is operational. This blanking interval may also be on the order of the duration of intracardiac activity or events that should be monitored (sensed and analyzed). Therefore, conventional blanking techniques tend to significantly compromise the ability to of the pacemaker to sense and analyze events of interest, especially during ATP therapy.

Secondly, certain cardioversion methods may require ATP pulses that have much higher amplitudes than pacing pulses used in conventional bradycardia therapy. These methods may also require that ATP pulse be delivered via high polarizing electrodes. Therefore, assuming an ATP pulse has a monophasic cathodal morphology similar to a conventional bradycardia pacing pulse, the polarization signal caused by the ATP pulse may be much greater than that caused by a conventional bradycardia pacing pulse. A large polarization signal can be disruptive to sensing from the stimulation electrode and possibly also from neighboring electrodes. One solution to this problem would be to lengthen the blanking interval and fast recharge interval. However, that would further compromise the ability of the pacemaker to effectively sense and analyze intracardiac signals during ATP therapy.

Thirdly, the monitoring of very low amplitude intracardiac signals that are produced during atrial or ventricular fibrillation requires that the pacemaker have a much higher amplification gain and/or lower sensing threshold setting than is typically required for detecting P-waves and R-waves in sinus rhythm. This tends to exacerbate both of the issues described above, because the more sensitive the amplifier the more prone it is to inadvertently sensing artifacts associated with a stimulation pulse, the fast recharge phase, and/or the blanking operation itself.

Consequently, there is a need for improved methods and arrangements that can be used to provide both cardiac stimulation pulses and effective intracardiac activity monitoring.

SUMMARY

The present invention provides improved methods and arrangements that can be used to provide both cardiac stimulation pulses and effective intracardiac activity monitoring.

Thus, for example, the above stated needs and others are met by a method for operating an implantable cardiac stimulation device, in accordance with certain exemplary implementations of the present invention. The method includes applying a substantially symmetrical multiphasic stimulation pulse waveform to a portion of a heart, and selectively sensing an electrical signal associated with intracardiac activity of the heart via a sensing mechanism that is operatively configured to significantly reject the multiphasic stimulation pulse waveform. The sensing and associated analysis of the intracardiac electric signal may occur simultaneous with the application of the multiphasic stimulation pulse waveform to the heart, and/or thereafter.

In certain implementations the multiphasic stimulation pulse waveform is a substantially symmetrical biphasic or triphasic pulse waveform that is provided during a desired stimulation period or moment. The multiphasic stimulation pulse waveform preferably has parameters that are selected to substantially reduce cross-talk effects in different conductive channels. The multiphasic stimulation pulse waveform may also have parameters that are selected to reduce polarization associated with an electrode-tissue interface within the heart. In certain implementations, the multiphasic stimulation pulse waveform is applied to the portion of the heart during antitachycardia pacing treatment, bradycardia pacing treatment, arrhythmia preventative pacing treatment, and/or other like pacing treatments.

In accordance with certain aspects of the present invention, the multiphasic stimulation pulse waveform is operatively configured to minimize an amount of energy provided through a direct current (DC) component and selected lower frequency components. Thus, the sensing mechanism may be operatively configured to reject, filter, attenuate, and/or otherwise ignore the energy that is carried by frequency components outside of a particular lower frequency range.

BRIEF DESCRIPTION OF THE DRAWINGS

Features and advantages of the described implementations can be more readily understood by reference to the following description taken in conjunction with the accompanying drawings.

DETAILED DESCRIPTION

Figure 1:
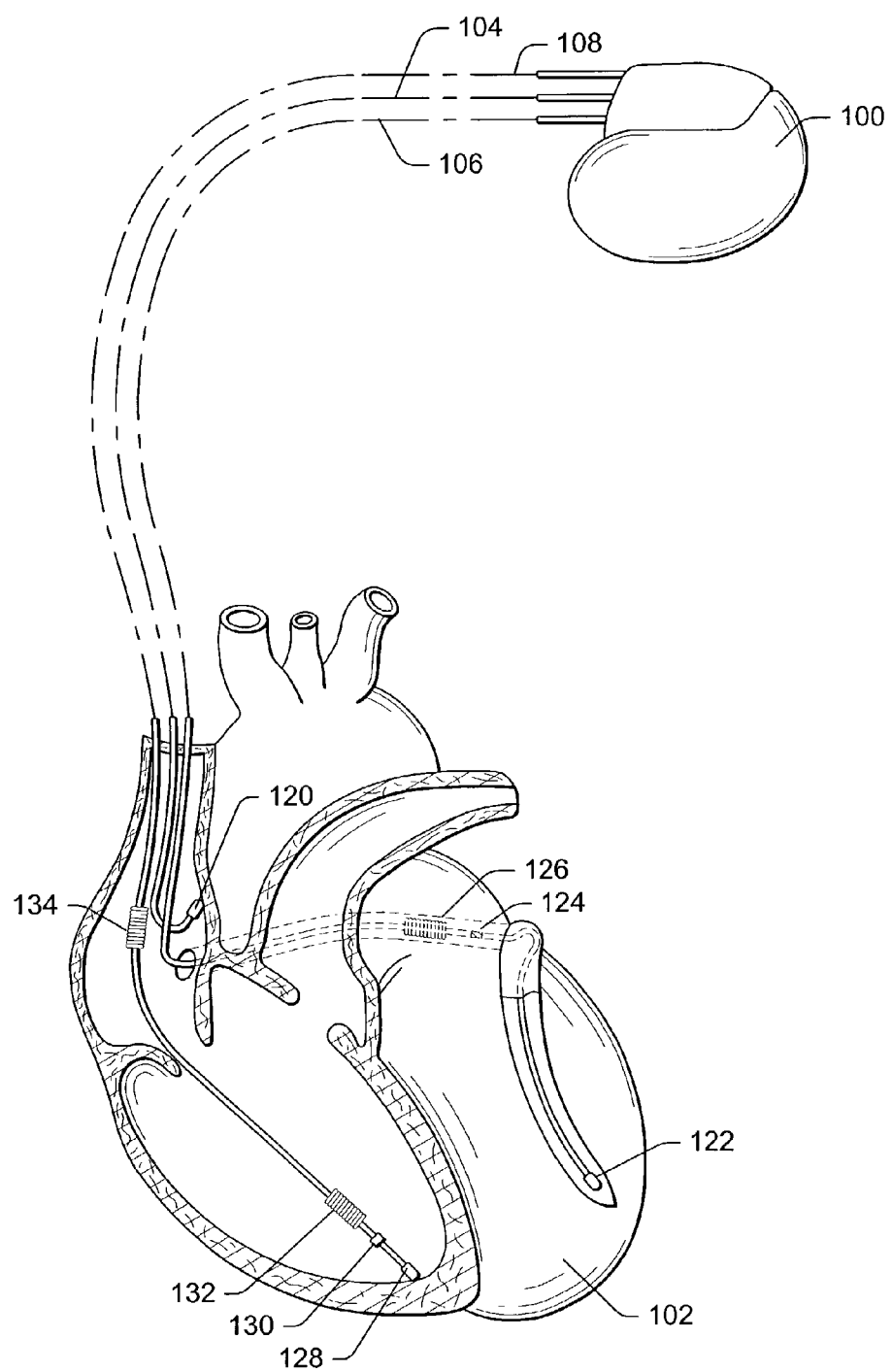
FIG. 1 is a simplified diagram illustrating an implantable stimulation device in electrical communication with at least three leads implanted into a patient's heart for delivering multi-chamber stimulation and shock therapy, in accordance with certain exemplary implementations of the present invention.

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

Different pulse waveforms deliver energy at different frequencies. Thus, it would be advantageous to design a pulse waveform that has minimal energy in a desired frequency band. In accordance with certain aspects of the present invention, certain stimulation pulse waveforms are provided that advantageously have very little energy in a selected passband associated with the sense amplifier(s), which are configured to sense and analyze intracardiac signals. Thus, stimulation pulses with certain morphologies will not significantly affect the operation of such amplifiers due to the minimal interference with the sensing and analysis of intracardiac signals.

Therefore, in accordance with certain implementations of the present invention, the improved stimulation pulse waveforms can be administered while, simultaneously, intracardiac signals are being sensed and analyzed. Hence, there may be no need for a blanking period. For example, certain stimulation pulse morphologies used during ATP essentially minimize or eliminate the need for blanking amplifiers, and allow for continuous sensing and analysis of intracardiac signals during the ATP therapy.

Additionally, as will be seen, the improved stimulation pulse waveforms have little, if any, net DC content. Thus, polarization at the lead-tissue interface will be greatly reduced. This reduction in polarization can facilitate continuous sensing from even the stimulation electrodes in certain situations. Furthermore, when the stimulation pulse waveforms have no net DC content, the fast recharge phase of the stimulation pulse may be significantly shortened or even eliminated.

Elimination or shortening of the blanking intervals and/or fast recharge phases associated with stimulation pulses is may also be beneficial in bi-atrial or bi-ventricular resynchronization therapy. When two chambers are substantially simultaneously stimulated, for example, blanking and recharge associated with the later stimulation pulse tends to interfere with sensing of the evoked response associated with the first pulse. Thus, eliminating or shortening of the blanking intervals and/or fast recharge phases can facilitate capture management during bi-atrial or bi-ventricular stimulation therapy.

U.S. Pat. No. 6,044,294, (Mortazavi et al.), discloses techniques that allow a pacemaker to measure the impedance of a patient's body without interfering with the operation of external cardiac monitoring equipment, such as, an electrocardiogram (ECG) machine. Mortazavi et al., teach that certain impedance measurement signals having multiphasic waveforms can be used by the pacemaker to measure the impedance of the patient's body. These multiphasic waveforms have no net DC component and result in a zero value in the ECG machine, following a second integration of the sensed cardiac signal.

Considering the methods and arrangements provided herein, it is noted that Mortazavi et al., do not disclose or otherwise suggest that multiphasic waveforms can be used for stimulation therapy. Additionally, Mortazavi et al. do not disclose or otherwise suggest that certain multiphasic waveforms can have frequency components that can be filtered, or otherwise rejected in some manner, by the sense amplifier(s) in the pacemaker. For these and other reasons, Mortazavi et al., do not recognize or consider the problems related to cardioversion and pacing therapies that are addressed by the present improved methods and arrangements.

Exemplary Stimulation Device

The techniques described below are intended to be implemented in connection with any stimulation device that is configured or configurable to stimulate or shock a patient's heart.

FIG. 1 shows an exemplary stimulation device 100 in electrical communication with a patient's heart 102 by way of three leads 104, 106, and 108, suitable for delivering multi-chamber stimulation and shock therapy. To sense atrial cardiac signals and to provide right atrial chamber stimulation therapy, stimulation device 100 is coupled to an implantable right atrial lead 104 having at least an atrial tip electrode 120, which typically is implanted in the patient's right atrial appendage.

To sense left atrial and ventricular cardiac signals and to provide left chamber pacing therapy, stimulation device 100 is coupled to a coronary sinus lead 106 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is designed to receive atrial and ventricular cardiac signals and to deliver left ventricular pacing therapy using at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. patent application Ser. No. 09/457,277, filed Dec. 8, 1999, entitled "A Self-Anchoring, Steerable Coronary Sinus Lead" (Pianca et al); and U.S. Pat. No. 5,466,254, "Coronary Sinus Lead with Atrial Sensing Capability" (Helland), which are incorporated herein by reference.

Stimulation device 100 is also shown in electrical communication with the patient's heart 102 by way of an implantable right ventricular lead 108 having, in this implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

Figure 2:
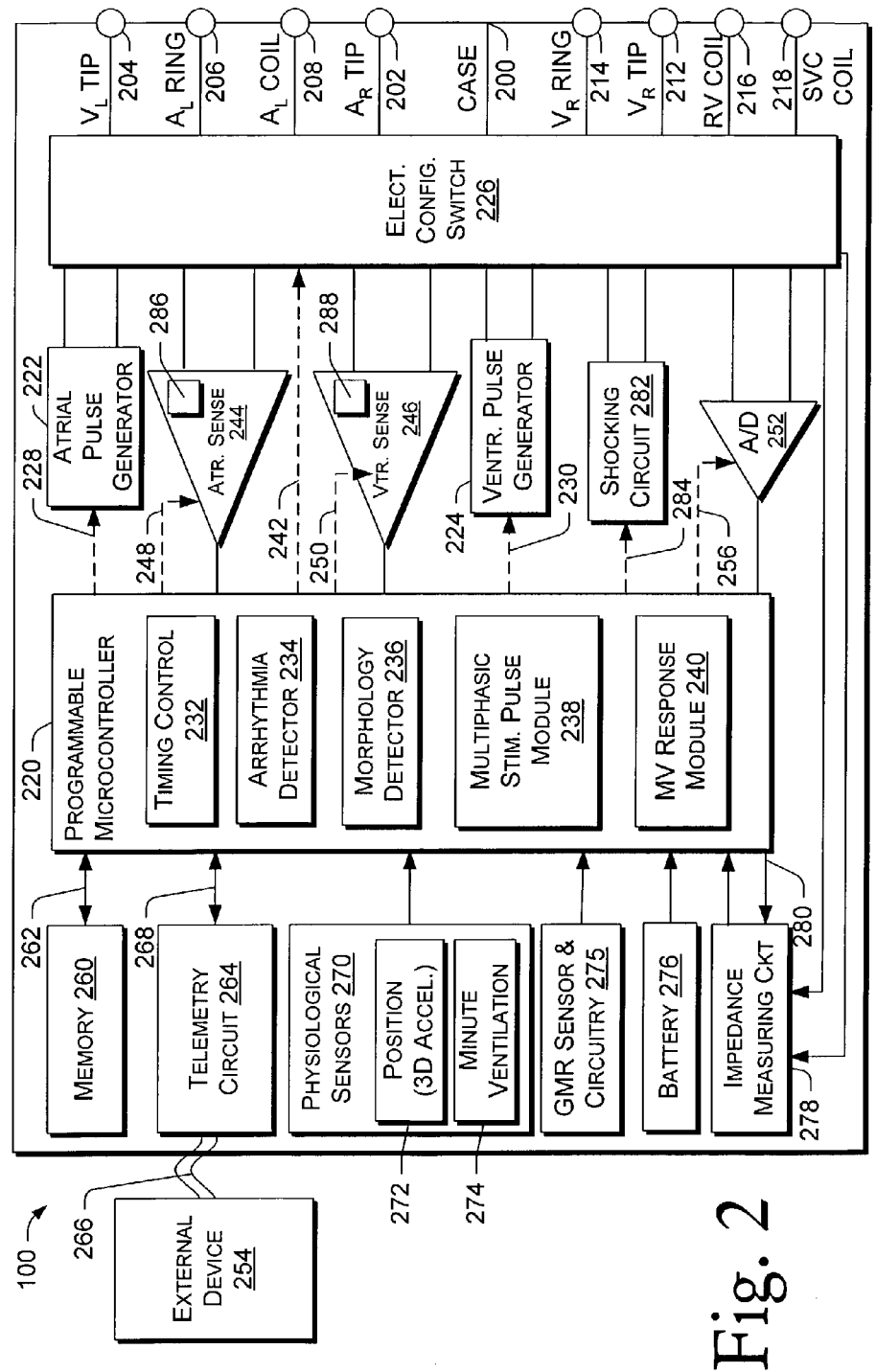
FIG. 2 is a functional block diagram of a multi-chamber implantable stimulation device illustrating basic elements that are configurable to provide multiphasic stimulation pulse waveforms to a heart during stimulation therapy, in accordance with certain exemplary implementations of the present invention.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry/logic in any desired combination to provide a device capable of treating the appropriate chamber(s) with cardioversion, defibrillation, and pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal ($A_R$ TIP) 202 adapted for connection to the atrial tip electrode 120. To achieve left chamber sensing, pacing, and shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular ring electrode 122, the left atrial tip electrode 124, and the left atrial coil electrode 126, respectively.

To support right chamber sensing, pacing, and shocking, the connector further includes a right ventricular tip terminal ($V_R$ TIP) 212, a right ventricular ring terminal ($V_R$ RING) 214, a right ventricular shocking terminal (RV COIL) 216, and an SVC shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their interrelationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, multiphasic stimulation pulse module 238, and a minute ventilation (MV) response module 240. These components can be utilized by the stimulation device 100 for determining desirable times to administer various therapies. The components 234–240 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. In this exemplary implementation, atrial sensing circuit 244 is illustrated as having a filtering mechanism 286. Similarly, ventricle sensing circuit 246 is illustrated as having a filtering mechanism 288.

The automatic gain control enables the device 100 to deal effectively with the difficult problem of sensing the low amplitude signal characteristics of atrial or ventricular fibrillation. For a complete description of a typical sensing circuit, the reader is directed to U.S. Pat. No. 5,573,550, entitled "Implantable Stimulation Device having a Low Noise, Low Power, Precision Amplifier for Amplifying Cardiac Signals" (Zadeh et al.). For a complete description of an automatic gain control system, the reader is directed to U.S. Pat. No. 5,685,315, entitled "Cardiac Arrhythmia Detection System for an Implantable Stimulation Device" (McClure et al.). Accordingly, the '550 and the '315 patents are hereby incorporated herein by reference.

The outputs of the atrial and ventricular sensing circuits 244 and 246 are connected to the microcontroller 220 which, in turn, is able to trigger or inhibit the atrial and ventricular pulse generators 222 and 224, respectively, in a demand fashion in response to the absence or presence of cardiac activity in the appropriate chambers of the heart. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. As used herein "sensing" is reserved for the noting of an electrical signal, and "detection" is the processing of these sensed signals, and noting the presence of an arrhythmia, for example. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

Advantageously, the data acquisition system 252 may be coupled to the microcontroller 220, or other detection circuitry, for detecting an evoked response from the heart 102 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 220 detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determines if capture has occurred.

Capture detection may occur on a beat-by-beat basis or on a sampled basis. A capture threshold search can desirably be performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The implementation of capture detection circuitry and algorithms are well known. See, for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Kleks et al.), all of which are hereby incorporated herein by reference. The type of capture detection system used is not critical to the described implementations.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy.

One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266. For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are incorporated herein by reference.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V—V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et. al), issued Dec. 19, 1995, which patent is hereby incorporated by reference.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected. Accordingly, the device 100 preferably employs lithium/silver vanadium oxide batteries, as is true for most (if not all) current devices.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 220 further controls a shocking circuit 282 by way of a control signal 284. The shocking circuit 282 generates shocking pulses of low (e.g., up to about 0.5 Joules), moderate (e.g., about 0.5—about 10 Joules), or high energy (e.g., about 11 to about 40 Joules), as controlled by the microcontroller 220.

Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (e.g., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of about 5 to about 40 Joules), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Multiphasic Stimulation Pulse Therapy

Figure 3:
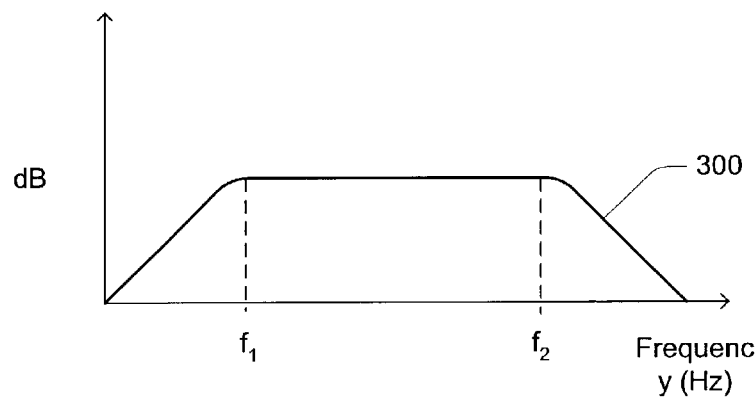
FIG. 3 is a graph depicting a passband frequency associated with an intracardiac sensing mechanism, in accordance with certain exemplary implementations of the present invention.

As mentioned in the previous section, atrial sensing circuit 244 is illustrated as having a filtering mechanism 286, and ventricle sensing circuit 246 is illustrated as having a filtering mechanism 288. With this in mind, FIG. 3 is a graph depicting an exemplary response curve 300 associated with filtering mechanism 286 and/or 288, in accordance with certain implementations of the present invention. As shown in this example, response curve 300 provides a passband from about $f_1$ to about $f_2$. Thus, frequency components in a sensed signal, which are outside of this passband, are attenuated accordingly. By way of example, in certain preferred implementations, the passband is between about $f_1$=18 Hz and about $f_2$=120 Hz, and the rise/fall of responsive curve 300 outside of the passband is about 40 dB/decade.

Figure 4:
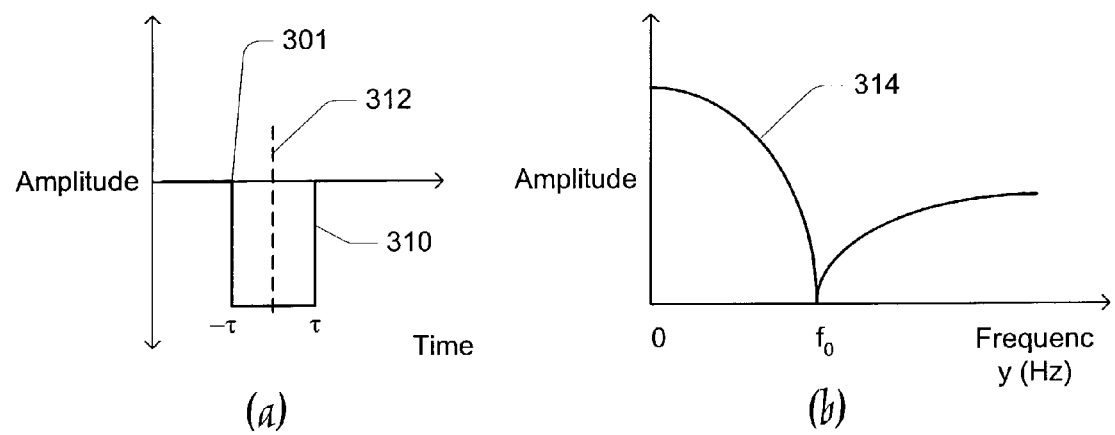
FIG. 4a and FIG. 4b are graphs depicting the time and frequency attributes, respectively, associated with a conventional monophasic stimulation pulse waveform, in accordance with certain exemplary implementations of the present invention.

FIG. 4a depicts an exemplary conventional stimulation pulse waveform 310. Here, stimulation pulse waveform 310 is a monophasic square wave that is generated during a desired stimulation period beginning with instance 311. Stimulation pulse waveform 310 is centered about a line 312. In this example, the polarity is negative. In other exemplary implementations the polarity can be reversed (i.e., positive). The duration of stimulation pulse waveform 310 is defined by a variable T. Thus, in this example, stimulation pulse waveform 310 has a duration of 2T. By way of example, in certain implementations designed to provide ATP therapy, T=0.5 milliseconds. Hence, the duration of stimulation pulse waveform 310 would be equal to 1.0 millisecond.

FIG. 4b is a graph that illustrates a portion of the corresponding amplitude of stimulation pulse waveform 310 as viewed in the frequency domain. Here, curve 314 has a sync-like shape, with a fairly high amplitude of DC (i.e., at 0 Hz). Furthermore, as shown, there is a significant amount of energy being carried by lower frequency components. Unfortunately, the DC component tends to cause a ringing (e.g., a damping oscillation) on the output of filtering mechanism 286 or 288. Further, the lower frequency components within the passband will likely be sensed. Ringing and interference, such as this, has lead to the use of blanking periods or intervals as previously described.

With this in mind, FIGS. 5a–b and FIGS. 6a–b depict exemplary improved, multiphasic stimulation pulse waveforms that have substantially reduced or non-existent DC components, and reduced amplitude lower frequency components. Consequently, in accordance with certain aspects of the present invention, the output from filtering mechanism 286 or 288 will be significantly unaffected by an applied multiphasic stimulation pulse waveform that is also sensed.

By using a multiphasic stimulation pulse waveform, in certain implementations, the blanking interval may be reduced or eliminated, the fast recharge may be reduced or eliminated, and polarization at lead-tissue interface may be reduced or effectively eliminated.

Figure 5:
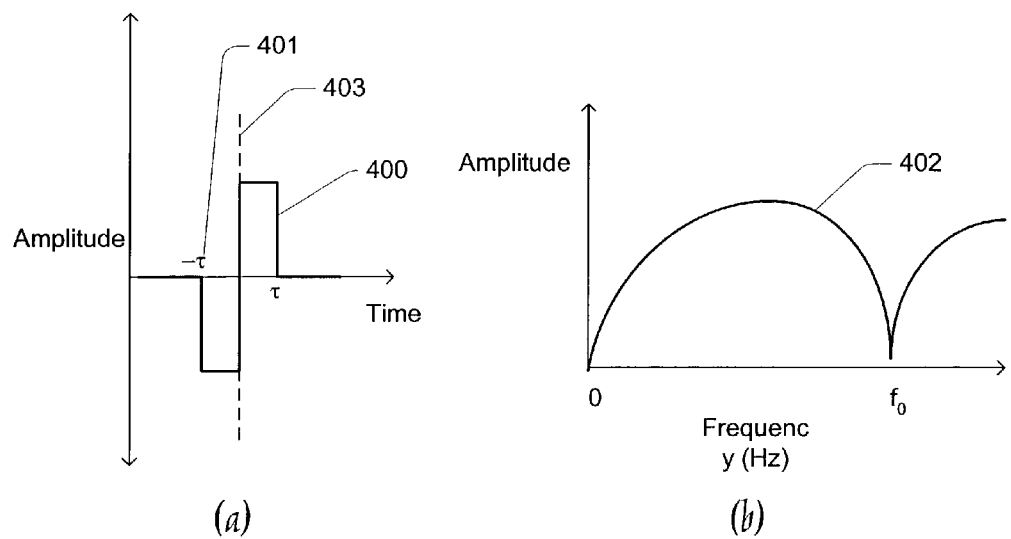
FIG. 5a and FIG. 5b are graphs depicting the time and frequency attributes, respectively, associated with a biphasic stimulation pulse waveform, in accordance with certain exemplary implementations of the present invention.

With reference to FIG. 5a, an exemplary multiphasic stimulation pulse waveform is depicted in the form of a biphasic stimulation pulse waveform 400. Biphasic stimulation pulse waveform 400 is generated during a desired stimulation period that begins at instance 401. Biphasic stimulation pulse waveform 400 is preferably symmetrical in shape. Here, for example, biphasic stimulation pulse waveform 400 is illustrated as being symmetrical about center line 403.

In this example, the polarity of biphasic stimulation pulse waveform 400 begins with a negative amplitude square wave having a duration of T, followed by a positive amplitude square wave also having a duration of T. The overall duration of exemplary biphasic stimulation pulse waveform 400 is therefore 2T. It is noted that the variable T and the amplitude of the square waves may be adjusted, as necessary for a given therapy. In certain implementations the polarity may be reversed such that a positive amplitude square wave precedes the negative amplitude square wave. As with the previous monophasic pulse waveform example, in certain implementations designed to provide ATP therapy, T=0.5 milliseconds. Hence, the overall duration of such an exemplary biphasic stimulation pulse waveform 400 would be equal to 1.0 millisecond.

While the examples depicted herein illustrated as being perfect square waves, it should be understood that other non-perfectly square waves may be used in the various multiphasic stimulation pulse waveforms.

FIG. 5b is a graph that illustrates a portion of the corresponding amplitude of biphasic stimulation pulse waveform 400 as viewed in the frequency domain. Here, curve 402 also has a sync-like shape, but without any significant DC component. Furthermore most of the energy is carried by higher frequency components.

Figure 6:
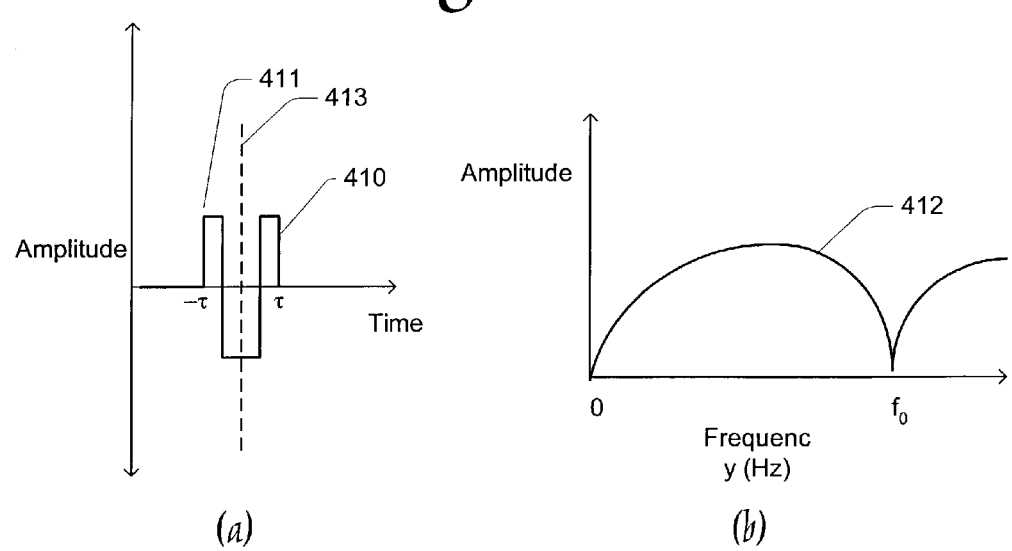
FIG. 6a and FIG. 6b are graphs depicting the time and frequency attributes, respectively, associated with a triphasic stimulation pulse waveform, in accordance with certain exemplary implementations of the present invention.

Reference is now made to FIG. 6a, which depicts an exemplary multiphasic stimulation pulse waveform in the form of a triphasic stimulation pulse waveform 410. Triphasic stimulation pulse waveform 410 is generated during a desired stimulation period that begins at instance 411. Triphasic stimulation pulse waveform 410 is also preferably symmetrical in shape. Here, for example, triphasic stimulation pulse waveform 410 is illustrated as being symmetrical about center line 412.

In this example, the polarity of triphasic stimulation pulse waveform 410 begins with a positive amplitude square wave having a duration of ½T, followed by a negative amplitude square wave having a duration of T, and then a positive amplitude square wave having a duration of ½T. The overall duration of exemplary triphasic stimulation pulse waveform 410 is therefore 2T. Again, it is noted that the variable T and the amplitude of the square waves may be adjusted, as necessary for a given therapy. The polarity may also be reversed in certain implementations.

As with the previous biphasic pulse waveform example, in certain implementations designed to provide ATP therapy, T=0.5 milliseconds. Hence, the overall duration of such an exemplary triphasic stimulation pulse waveform 410 would be equal to 1.0 millisecond.

In FIG. 6b, a graph is provided to illustrate a portion of the corresponding amplitude of triphasic stimulation pulse waveform 410 as viewed in the frequency domain. Here, curve 412, which is sync-like in shape, does not include any significant DC component, and illustrates that most of the energy is once again carried by higher frequency components.

Figure 7:
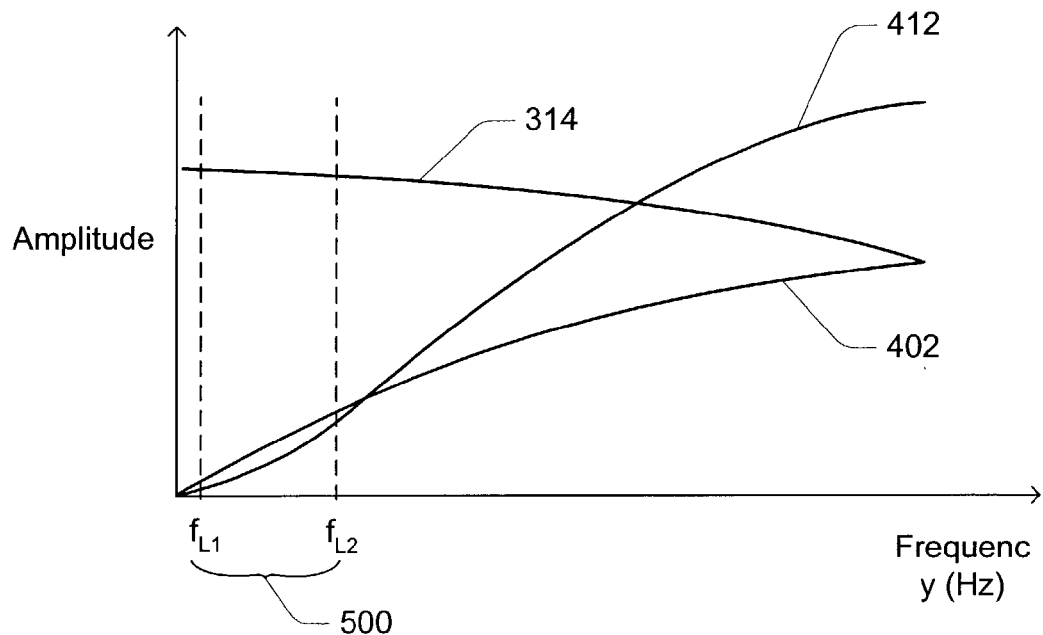
FIG. 7 is a graph depicting a comparison of frequency attributes associated with monophasic, biphasic and triphasic stimulation pulse waveforms, as in FIGS. 4a, 5a and 6a, respectively, in accordance with certain exemplary implementations of the present invention.

In FIG. 7, a comparison graph is provided, which shows a portion of the amplitude spectra of the previously illustrated exemplary monophasic, biphasic and triphasic stimulation pulse waveforms, with T=0.5 milliseconds. Again, line 314 represents the amplitude spectra of monophasic stimulation pulse waveform 310, line 402 represents the amplitude spectra of biphasic stimulation pulse waveform 400, and line 412 represents the amplitude spectra of triphasic stimulation pulse waveform 410. A lower frequency band 500 that extends from $f_{L1}$ to $F_{L2}$ is also depicted to further illustrate that the multiphasic stimulation pulse waveforms carry only a fraction of their respective energy within lower frequency band 500 when compared to the monophasic stimulation pulse waveform.

Figure 8:
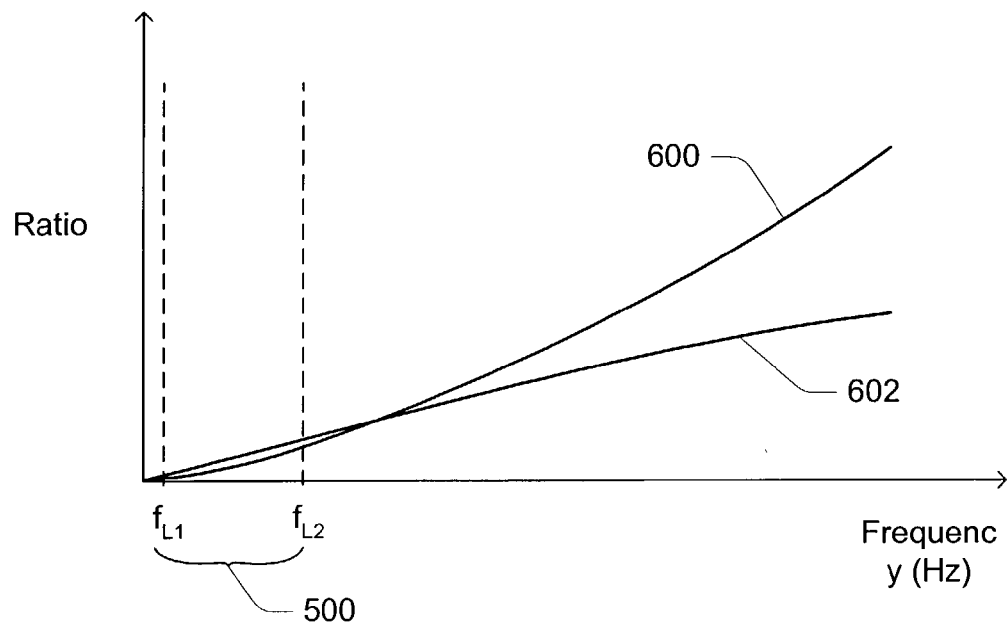
FIG. 8 is a graph depicting a comparison of ratios of frequency attributes associated with monophasic, biphasic and triphasic stimulation pulse waveforms, as in FIGS. 4a, 5a and 6a, respectively, in accordance with certain exemplary implementations of the present invention.

Indeed, FIG. 8 is graph that illustrates certain comparative ratios associated with the multiphasic verses monophasic stimulation pulse waveform amplitude spectra. Line 600 represents an exemplary ratio of the biphasic stimulation pulse waveform amplitude spectra to the monophasic stimulation pulse waveform amplitude spectra. Line 602 represents an exemplary ratio of the triphasic stimulation pulse waveform amplitude spectra to the monophasic stimulation pulse waveform amplitude spectra.

By way of example, in certain exemplary implementations, lower frequency band 500 extends from $f_{L1}$=18 Hz to $F_{L2}$=120 Hz. Thus, with T=0.5 milliseconds, at 60 Hz the biphasic stimulation pulse waveform has an amplitude in the frequency band that is about eleven times lower than that of the monophasic stimulation pulse waveform. Similarly at 60 Hz the triphasic stimulation pulse waveform has an amplitude in the frequency band that is about twenty eight times lower than that of the monophasic stimulation pulse waveform. If T is reduced to 0.25 milliseconds, then the biphasic stimulation pulse waveform will have an amplitude in the frequency band that is about twenty one times lower than that of the monophasic stimulation pulse waveform, and the triphasic stimulation pulse waveform will have an amplitude in the frequency band that is about one hundred thirteen times lower than that of the monophasic stimulation pulse waveform.

It should be understood, however, that the multiphasic stimulation pulse waveforms may not stimulate the targeted portion of heart as efficiently as might the monophasic stimulation pulse waveform. Therefore, the multiphasic stimulation pulse waveforms may require that the amplitude be increased moderately, e.g., by a factor of about 2. Nevertheless, significant rejection of these increased amplitude pulses by the filtering mechanism can still be achieved. It should also be understood that the shape and/or polarity presented in the exemplary multiphasic stimulation pulse waveforms may be altered in other implementations. Furthermore, the multiphasic stimulation pulse waveform may have more than two or three phases.

With reference to FIG. 2, those skilled in the art will recognize that multiphasic stimulation pulse waveforms may be generated by either atrial pulse generator 222, ventricle pulse generator 224, and/or shocking circuit 282, as required to support a specific cardiac therapy. For example, for ATP therapy, atrial pulse generator 222 can be configured to generate a monophasic stimulation pulse waveform of certain duration, amplitude and polarity as controlled by microcontroller 220 via line 228. Timing control module 232 can be configured to cause the electrode configuration switch 74, via line 242, to selectively switch the polarity of the monophasic stimulation pulse waveform generated by atrial pulse generator 70 at certain instances within the duration of the pulse waveform. This produces a multiphasic stimulation pulse waveform that can be selectively applied to the patient's heart through the appropriate leads/electrodes depending on the cardiac therapy and operating mode (e.g., unipolar or bipolar).

CONCLUSION

Although some preferred implementations of the various methods and arrangements of the present invention have been illustrated in the accompanying Drawings and described in the foregoing Detailed Description, it will be understood that the invention is not limited to the exemplary embodiments disclosed, but is capable of numerous rearrangements, modifications and substitutions without departing from the spirit of the invention as set forth and defined by the following claims.

What is claimed is:

1. A method for operating an implantable cardiac stimulation device, the method comprising:
applying a substantially symmetrical, multiphasic pacing pulse waveform to a portion of a heart, wherein an amplitude of the pacing pulse waveform at a first group of frequency components of the pacing pulse waveform is less than the amplitude of the pacing pulse waveform at a second group of frequency components of the pacing pulse waveform; and
selectively sensing an electrical signal associated with intracardiac activity of the heart via a sensing mechanism that is operatively configured to significantly reject the multiphasic pacing pulse waveform by attenuating the amplitude of the pacing pulse waveform at the second group of frequency components.

2. The method as recited in claim 1, wherein the multiphasic pacing pulse waveform is a substantially symmetrical biphasic pulse waveform.

3. The method as recited in claim 1, wherein the multiphasic pacing pulse waveform is a substantially symmetrical triphasic pulse waveform.

4. The method as recited in claim 1, wherein the multiphasic pacing pulse waveform is a substantially multiphasic square waveform.

5. The method as recited in claim 1, wherein the multiphasic pacing pulse waveform has parameters that are selected to substantially reduce cross-talk effects associated with at least one electrode configured to apply the multiphasic pacing pulse waveform to the portion of the heart and at least one electrode configured to sense the electrical signal associated with intracardiac activity of the heart.

6. The method as recited in claim 1, wherein the multiphasic pacing pulse waveform has parameters that are selected to reduce polarization associated with an electrode-tissue interface within the heart.

7. The method as recited in claim 1, wherein applying the substantially symmetrical multiphasic pacing pulse waveform to the portion of the heart further comprises selectively applying the multiphasic pacing pulse waveform to the portion of the heart during at least one type of pacing treatment selected from a group of different types of pacing treatments comprising an antitachycardia pacing treatment, a bradycardia pacing treatment, and an arrhythmia preventative pacing treatment.

8. The method as recited in claim 1, wherein the implantable cardiac stimulation device comprises at least one unipolar lead having at least one electrode that is electrically coupled to the heart.

9. The method as recited in claim 1, wherein the implantable cardiac stimulation device comprises at least one bipolar lead having at least one electrode that is electrically coupled to the heart.

10. The method as recited in claim 1, wherein the multiphasic pacing pulse waveform is operatively configured to minimize an amount of energy provided through a direct current (DC) component and the first group of frequency components, and wherein the sensing mechanism is operatively configured not to attenuate energy associated with the first group of frequency components in the sensed electrical signal.

11. The method as recited in claim 10, wherein the sensing mechanism comprises a filtering mechanism that is operatively configured to attenuate the energy in the second group of frequency components in the sensed electrical signal.

12. The method as recited in claim 11, wherein the filtering mechanism comprises a passband filter.

13. The method as recited in claim 12, wherein the passband filter provides a passband between about 18 Hz and about 120 Hz.

14. An implantable cardiac rhythm management device comprising:
means for applying a substantially symmetrical, multiphasic pacing pulse waveform to a portion of a heart, wherein an amplitude of the pacing pulse waveform at a first group of frequency components of the pacing pulse waveform is less than the amplitude of the pacing pulse waveform at a second group of frequency components of the pacing pulse waveform;

means for selectively sensing an electrical signal associated with intracardiac activity of the heart; and means for analyzing the sensed electrical signal and significantly ignoring the second group of frequency components of the multiphasic pacing pulse waveform within the sensed electrical signal.

15. The cardiac rhythm management device as recited in claim 14, wherein the multiphasic pacing pulse waveform is a substantially symmetrical biphasic pulse waveform.

16. The cardiac rhythm management device as recited in claim 14, wherein the multiphasic pacing pulse waveform is a substantially symmetrical triphasic pulse waveform.

17. The cardiac rhythm management device as recited in claim 14, wherein the multiphasic pacing pulse waveform is a substantially square waveform.

18. The cardiac rhythm management device as recited in claim 14, wherein the multiphasic pacing pulse waveform has parameters that are selected to substantially reduce cross-talk associated with the application of the multiphasic pacing pulse waveform.

19. The cardiac rhythm management device as recited in claim 14, wherein the multiphasic pacing pulse waveform has parameters that are selected to reduce an amount of polarization associated with the application of the multiphasic pacing pulse waveform.

20. An implantable cardiac stimulation device comprising:

a pulse generator that is operative to generate a substantially symmetrical, multiphasic pacing pulse waveforms, wherein an amplitude of the pacing pulse waveform at a first group of frequency components of the pacing pulse waveform is less than the amplitude of the pacing pulse waveform at a second group of frequency components of the pacing pulse waveform;

at least one lead connected to the pulse generator, and adapted to deliver the multiphasic pacing pulse waveform to a heart; and detection circuitry that is operative to sense an electrical signal associated with intracardiac activity of the heart, wherein the detection circuitry is operatively configured to significantly reject the multiphasic pacing pulse waveform at the second group frequency components.

* * * * *